United States Patent [19]
Benjamin, Jr.

[11] 4,015,595
[45] Apr. 5, 1977

[54] PHOTOPLETHYSMOGRAPHS

[76] Inventor: J. Malvern Benjamin, Jr., c/o Bionic Instruments, Inc., 221 Rock Hill Road, Bala Cynwyd, Pa. 19004

[22] Filed: Sept. 15, 1975

[21] Appl. No.: 613,301

[52] U.S. Cl. .................. 128/2.05 V; 128/2.05 P
[51] Int. Cl.² ................................ A61B 5/02
[58] Field of Search .......... 128/2.05 V, 2.05 P, 128/2.05 T, 2 L, 2 A; 356/39

[56] References Cited
UNITED STATES PATENTS

| | | | |
|---|---|---|---|
| 3,103,214 | 9/1963 | Smith | 128/2.05 P |
| 3,167,658 | 1/1965 | Richter | 128/2.05 P X |
| 3,359,975 | 12/1967 | Sherman | 128/2 L |
| 3,638,640 | 2/1972 | Shaw | 128/2 L |
| 3,698,382 | 10/1972 | Howell | 128/2.05 V X |
| 3,787,119 | 1/1974 | Rybak | 356/39 X |
| 3,910,701 | 10/1975 | Henderson et al. | 356/39 |
| 3,916,205 | 10/1975 | Kleinerman | 356/39 X |
| 3,923,397 | 12/1975 | Shuck | 356/39 |

Primary Examiner—Kyle L. Howell
Attorney, Agent, or Firm—Smith, Harding, Earley & Follmer

[57] ABSTRACT

A photoplethysmograph probe including a light source, a photo-sensitive cell and a light control film positioned in front of the light source and photo-sensitive cell for collimating the light emitted from the light source and reflected back to the photo-sensitive cell.

7 Claims, 3 Drawing Figures

PHOTOPLETHYSMOGRAPHS

BACKGROUND OF THE INVENTION

A photoplethysmograph is a device used for the measurement of a peripheral pulsatile blood flow. It senses blood flow by means of a probe placed on the surface of the skin of any part of the body. The probe contains a tiny light source and a specially selected photo-sensitive cell that responds to light absorbed by the arterial blood in the peripheral vascular bed over which the sensor is placed. Since the cell responds to the light absorbed by the blood in its view, the amount of pulsating light it registers is proportional to the amount of pulsating arterial blood in its field.

In practice, however, the amplitude of electrical signal produced by the photo-sensitive cell not only varies with the amount of pulsation of blood, but also varies with the pressure of application of the probe to the skin surface. As the pressure is gradually increased, at first the amplitude of the signal gradually rises. It reaches a maximum, and then, with further increases in pressure, once again diminishes until it finally drops off to zero. The drop-off of signal beyond the maximum point as the pressure increases is easily explained in terms of the high pressure's squeezing the blood vessels closed and thus actually cutting off the blood flow. The increase in amplitude at first with increasing pressure is caused by changes in the amount of steady state static light returned to the photocell. It is the average amount of light returned to the photocell that establishes the average resistance of the cell (the operating point) and thus the average gain or sensitivity of the cell as regards the pulsatile signal which is being measured.

One of the problems involved in the photoplethysmographic pickup of the blood flow pulse is that variations in the amount of scattered light reaching the photocell cause variations in the operating point of the photocell. This adversely affects the accuracy of the measurement.

Another problem associated with the photoplethysmographic pickup of the blood flow pulse is artifactual noise produced by motion of the photo-sensitive cell and light source with respect to the pickup site. If the site is illuminated by broad spectrum "white" light, all of this light will be reflected from the structures within the tissue and as these structures move with respect to the pickup, noise will be generated which adversely affects the accuracy of the measurement.

SUMMARY OF THE INVENTION

It is the general object of this invention to provide improvements in photoplethysmographs and, more particularly, to improve the accuracy of the photoplethysmographic pickup of the blood flow pulse.

In accordance with one feature of the invention means are provided for holding the operating point of the photocell constant by overcoming the adverse affects of the scattered light reaching the photocell. To this end, the amount of scattered light reaching the photocell can be made closer to constant by placing in front of the photocell and light source a small piece of light control film. This film has the effect of collimating the light thereby to make the sensor more nearly dependent only upon the light beam directly reflected from the pulsating blood field.

In accordance with another feature of the invention, the artifactual noise produced by motion of the photocell and light source with respect to the pickup site is reduced by the provision of the photoplethysmographic probe in which the light is emitted in a narrow band of wave lengths centering in the green. By this construction only green light will be absorbed by the oxygenated arterial blood and it is this arterial blood pulsing through the vessels which produces the signals that are desired. Specifically, oxygenated hemoglobin reflects light maximally at 640 nanometers (red) and therefore absorbs maximally at the complimentary color, green. Thus, if light in and around the green wave lengths is transmitted into the structure, the motion artifact will be minimized.

DETAILED DESCRIPTION OF THE PREFERRED EMBODIMENTS OF THE INVENTION

Figure 1:
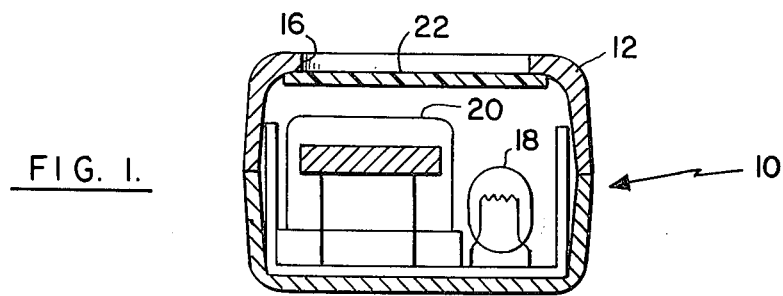
FIG. 1 is a sectional view of a photoplethysmographic probe in accordance with the invention.
Figure 2:
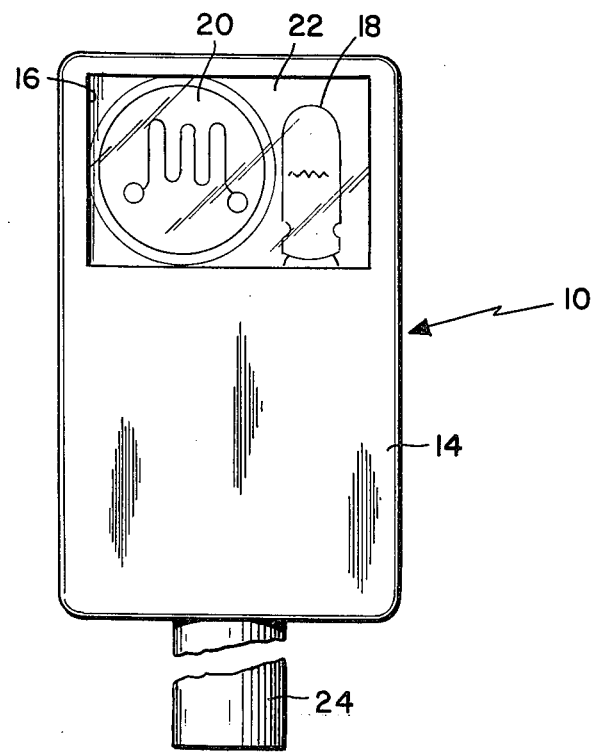
FIG. 2 is a plan view of the probe shown in FIG. 1.

The photoplethysmographic probe in accordance with the invention is indicated generally at 10 and comprises a casing 12 having a generally rectangular bottom side 14 provided with a window 16. A light source 18 is mounted within the casing 12 to overlie the window 16 so that it directs light through the window 16 toward a field to be measured. A photo-sensitive cell 20 is mounted within the casing 12 adjacent the light source 18 so that it responds to light reflected from the field to be measured and passing through the window 16. The cell 20 is preferably a cadmium selenide photocell. In the form of the invention shown in FIGS. 1 and 2, the light source 18 is a miniature incandescent lamp. A flexible multi-conductor cable 24 extends from the casing 12 and contains various conductors for the electrical circuitry to be described hereafter.

In accordance with a feature of the invention, a light control film 22 is mounted within the casing 12 to extend across the window 16. Accordingly, the light emitted from the light source 18 passes through the light control film 22 to the field to be measured and light is reflected from this field back through the light control film 22 to the photo-sensitive cell 20. The light control film 22 is made of a 0.030 inch thick clear cellulose acetate butyrate film. Light control film of this type is known in the art and is commercially available, such as from the Edmund Scientific Company. The light control film 22 has the effect of collimating the light passing therethrough to thereby make the photo-sensitive cell 20 more nearly dependent only upon the light beam directly reflected from the field being measured. Thus, the amount of scattered light reaching the photo-sensitive cell is made closer to constant. This serves to hold the operating point of the photo-sensitive cell more constant which improves the accuracy of the measurement.

In accordance with another feature of the invention, the light source 18 is constructed to emit light in a narrow band of green wave lengths. This may be achieved by the use of an appropriate light emitting diode or a miniature incandescent lamp with an appropriate filter. By this construction, the artifactual noise produced by motion of the photo-sensitive cell 20 and light source 18 with respect to the pickup site is reduced. This design avoids the problems resulting from illuminating the pickup site by "white" light in which case all of this light will be reflected from the structures within the tissue causing noise generation as these structures move with respect to the pickup. At the same time, only the source light will be reflected by the oxygenated arterial blood and it is this arterial blood pulsing through the vessels which produces the signal that is desired in a photoplethysmographic pickup.

Figure 3:
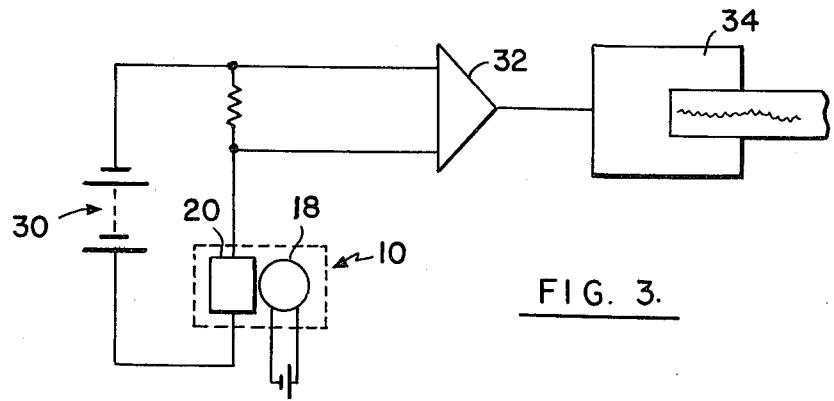
FIG. 3 is a schematic illustration of the electrical circuitry of a photoplethysmograph incorporating the probe shown in FIGS. 1 and 2.

In FIG. 3, there is provided a schematic illustration of the electrical circuitry of a photoplethysmograph incorporating a probe in accordance with the invention. There is shown a probe 10 provided with a light source 18 and a photo-sensitive cell 20. The light source 18 may be an incandescent lamp or it may be designed to emit light in a narrow band of green wave lengths. There is also provided a suitable power source 30, an amplifier 32 and a chart recorder 34. The electrical output from the photo-sensitive cell 20 is delivered to the amplifier 32 which delivers an amplified signal to operate the chart recorder 34.

In the use of the probe in accordance with the invention for the measurement of peripheral pulsatile blood flow, the sensing probe 10 is applied to the skin of the patient above the field to be measured. The light source 18 emits light and the photo-sensitive cell 20 responds to the light absorbed by the arterial blood in the peripheral vascular bed over which the probe 10 is placed. Since the photo-sensitive cell 20 responds linearly to the light reflected from the blood in its view, the amount of pulsating light it registers is directly proportional to the amount of pulsating arterial blood. The photo-sensitive cell 20 delivers its output to the amplifier 32 which amplifies the signal and transmits it to the chart recorder 34 which records the variations in the pulse amplitudes to provide a written record which can be analyzed to determine the blood flow through the field being measured.

I claim:

1. A probe for use with a photoplethysmograph for the measurement of peripheral pulsatile blood flow comprising:
   a casing having a window therein,
   a light source and a photo-sensitive cell mounted in said casing to overlie said window,
   said light source being arranged to direct light through said window,
   said photo-sensitive cell being arranged adjacent said light source to respond to light passing through said window as it is reflected from a field in line with said light source, and
   a light control film mounted to extend across said window for collimating the light emitted from said light source to direct the same toward said field and for collimating the light reflected to said photo-sensitive cell and passing through said window.

2. A probe according to claim 1 wherein said light control film is made of a clear cellulose acetate butyrate film.

3. A probe according to claim 2 wherein said light source comprises an incandescent lamp.

4. A probe according to claim 1 wherein said light source comprises an incandescent lamp.

5. A probe according to claim 1 wherein said light source is constructed to emit light in a narrow band of green wave lengths.

6. A probe according to claim 2 wherein said light source is constructed to emit light in a narrow band of green wave lengths.

7. A probe for use with a photoplethysmograph for the measurement of peripheral pulsatile blood flow by application to the surface of the patient's skin comprising:
   a casing having a window therein,
   a light source and a photo-sensitive cell mounted in said casing to overlie said window,
   said light source being arranged to direct light through said window to a field of blood,
   said photo-sensitive cell being arranged adjacent said light source to respond to light reflected from a field of blood in line with said light source, and
   said light source being constructed to emit light in a narrow band of green wave lengths so that substantially all of said light is absorbed by the blood so as to minimize the motion artifact.

* * * * *